(12) United States Patent
Graham et al.

(10) Patent No.: US 7,676,865 B2
(45) Date of Patent: Mar. 16, 2010

(54) TRANSFERABLE PATIENT CARE EQUIPMENT SUPPORT

(75) Inventors: Mark Alan Graham, Springboro, OH (US); Michael E. Cerimele, Indianapolis, IN (US); David C. Newkirk, Lawrenceburg, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 951 days.

(21) Appl. No.: 11/397,013

(22) Filed: Apr. 3, 2006

(65) Prior Publication Data

US 2006/0242763 A1 Nov. 2, 2006

Related U.S. Application Data

(63) Continuation-in-part of application No. PCT/US2004/033469, filed on Oct. 12, 2004.

(60) Provisional application No. 60/510,756, filed on Oct. 13, 2003, provisional application No. 60/776,768, filed on Feb. 24, 2006.

(51) Int. Cl.
  *A61G 7/05* (2006.01)
  *A47C 21/00* (2006.01)
(52) U.S. Cl. ............... 5/503.1; 5/600; 5/658; 248/158; 248/159
(58) Field of Classification Search ............ 5/600, 5/658, 503.1, 81.1 R; 248/158, 159, 125.1, 248/125.8
See application file for complete search history.

(56) References Cited

U.S. PATENT DOCUMENTS

| | | | |
|---|---|---|---|
| 383,815 A | 5/1888 | Kilborn | |
| 1,290,809 A | 1/1919 | Truax | |
| 1,490,650 A | 4/1924 | Wagner | |
| 1,919,114 A | 7/1933 | Ley | |
| 2,470,524 A | 5/1949 | Scudder | |
| 2,497,425 A | 2/1950 | Terry | |
| 2,673,771 A | 3/1954 | Krewson | |
| 2,696,963 A | 12/1954 | Sheperd | |
| 3,004,743 A | 10/1961 | Wenger | |
| 3,213,877 A | 10/1965 | May et al. | |
| 3,431,937 A | 3/1969 | Hettlinger et al. | |

(Continued)

FOREIGN PATENT DOCUMENTS

DE 92 04 321.6 U1 7/1992

(Continued)

OTHER PUBLICATIONS

"Pump Star User's Manual", The Headwall Company, Modular Services Company, Dec. 22, 2005, 11 pages.

(Continued)

*Primary Examiner*—Robert G Santos
(74) *Attorney, Agent, or Firm*—Barnes & Thornburg LLP (57) ABSTRACT

A patient care equipment support is transferable between a first device having a first tapered socket and a second device having a second tapered socket. The equipment support includes an equipment supporting portion configured to support patient care equipment and a post coupled to the equipment supporting portion and extending generally downwardly therefrom. The post has first and second tapered portions. The first tapered portion is configured for receipt in the first tapered socket and the second tapered portion being configured for receipt in the second tapered socket.

21 Claims, 3 Drawing Sheets

U.S. PATENT DOCUMENTS

| | | | |
|---|---|---|---|
| 3,552,577 A | 1/1971 | Latham, Jr. |
| 3,674,294 A | 7/1972 | Kirkham |
| 3,709,556 A | 1/1973 | Allard et al. |
| 3,814,023 A | 6/1974 | Stantial |
| 4,005,844 A | 2/1977 | Richmond |
| 4,094,484 A | 6/1978 | Galione |
| 4,113,222 A | 9/1978 | Frinzel |
| 4,190,224 A | 2/1980 | LeBlanc et al. |
| 4,225,104 A | 9/1980 | Larson |
| 4,262,874 A | 4/1981 | Seigh |
| D260,816 S | 9/1981 | Zissimopoulos et al. |
| 4,339,104 A | 7/1982 | Weidman |
| 4,378,014 A | 3/1983 | Elkow |
| 4,489,454 A | 12/1984 | Thompson |
| 4,511,157 A | 4/1985 | Wilt, Jr. |
| 4,511,158 A | 4/1985 | Varga et al. |
| 4,559,036 A | 12/1985 | Wunsch |
| 4,600,209 A | 7/1986 | Kerr, Jr. |
| 4,616,797 A | 10/1986 | Cramer |
| D289,604 S | 5/1987 | Gallant et al. |
| 4,691,397 A | 9/1987 | Netzer |
| 4,718,892 A | 1/1988 | Yung-Ho |
| 4,725,027 A | 2/1988 | Bekanich |
| 4,729,576 A | 3/1988 | Roach |
| 4,738,369 A | 4/1988 | Desjardins |
| 4,744,536 A | 5/1988 | Bancalari |
| 4,756,706 A | 7/1988 | Kerns et al. |
| 4,795,122 A | 1/1989 | Petre |
| 4,879,798 A | 11/1989 | Petre |
| 4,892,279 A | 1/1990 | Lafferty et al. |
| 4,901,967 A | 2/1990 | Petre |
| 4,905,882 A | 3/1990 | Ross |
| 4,905,944 A | 3/1990 | Jost et al. |
| 4,925,444 A | 5/1990 | Orkin et al. |
| 4,945,592 A | 8/1990 | Sims et al. |
| 4,966,340 A | 10/1990 | Hunter |
| 4,969,768 A | 11/1990 | Young |
| 4,997,150 A | 3/1991 | Mardollo |
| 5,016,307 A | 5/1991 | Rebar |
| 5,078,349 A | 1/1992 | Smith |
| 5,083,807 A | 1/1992 | Bobb et al. |
| 5,094,418 A | 3/1992 | McBarnes, Jr. et al. |
| 5,110,076 A | 5/1992 | Snyder et al. |
| 5,112,019 A | 5/1992 | Metzler et al. |
| 5,125,607 A | 6/1992 | Pryor |
| 5,135,191 A | 8/1992 | Schmuhl |
| 5,149,036 A | 9/1992 | Sheehan |
| 5,207,642 A | 5/1993 | Orkin et al. |
| 5,219,139 A | 6/1993 | Hertzler et al. |
| 5,224,681 A | 7/1993 | Lundstrom |
| 5,306,109 A | 4/1994 | Kreuzer et al. |
| 5,319,816 A | 6/1994 | Ruehl |
| 5,326,059 A | 7/1994 | Pryor et al. |
| 5,337,992 A | 8/1994 | Pryor et al. |
| 5,344,169 A | 9/1994 | Pryor et al. |
| 5,366,191 A | 11/1994 | Bekanich |
| 5,400,995 A | 3/1995 | Boyd |
| 5,407,163 A | 4/1995 | Kramer et al. |
| 5,421,548 A | 6/1995 | Bennett et al. |
| 5,527,125 A | 6/1996 | Kreuzer et al. |
| 5,527,289 A | 6/1996 | Foster et al. |
| 5,556,065 A | 9/1996 | Wadley |
| 5,588,166 A | 12/1996 | Burnett |
| 5,618,090 A | 4/1997 | Montague et al. |
| 5,636,823 A | 6/1997 | Boyd |
| 5,647,491 A | 7/1997 | Foster et al. |
| 5,657,884 A | 8/1997 | Zilincar, III |
| 5,699,988 A | 12/1997 | Boettger et al. |
| 5,704,577 A | 1/1998 | Gordon |
| 5,857,685 A | 1/1999 | Phillips et al. |
| 5,876,016 A | 3/1999 | Urban et al. |
| 5,878,536 A | 3/1999 | Demmitt et al. |
| 5,898,961 A | 5/1999 | Ambach et al. |
| 5,924,658 A | 7/1999 | Shiery et al. |
| 5,966,760 A | 10/1999 | Gallant et al. |
| 5,987,670 A | 11/1999 | Sims et al. |
| 6,056,249 A | 5/2000 | Fillon, Jr. |
| 6,073,285 A | 6/2000 | Ambach et al. |
| 6,109,572 A | 8/2000 | Urban et al. |
| 6,155,743 A | 12/2000 | Chen |
| 6,170,102 B1 | 1/2001 | Kreuzer |
| 6,179,260 B1 | 1/2001 | Ohanian |
| 6,182,662 B1 | 2/2001 | McGhee |
| 6,213,481 B1 | 4/2001 | Marchese et al. |
| 6,231,016 B1 | 5/2001 | Slone |
| 6,375,133 B1 | 4/2002 | Morrow |
| 6,390,311 B1 | 5/2002 | Belokin |
| 6,434,329 B1 | 8/2002 | Dube et al. |
| 6,585,206 B2 | 7/2003 | Metz et al. |
| 6,601,860 B2 | 8/2003 | Potter |
| 6,619,599 B2 | 9/2003 | Elliott et al. |
| 6,708,991 B1 | 3/2004 | Ortlieb |
| 6,725,483 B2 | 4/2004 | Gallant et al. |
| 7,040,057 B2 | 5/2006 | Gallant et al. |
| 7,065,811 B2 | 6/2006 | Newkirk et al. |
| 7,065,812 B2 | 6/2006 | Newkirk et al. |
| 7,216,382 B2* | 5/2007 | Newkirk et al. ............ 5/600 |
| 7,254,850 B2* | 8/2007 | Newkirk et al. ............ 5/600 |
| 7,418,749 B2* | 9/2008 | Graham et al. ............ 5/503.1 |
| 2004/0199996 A1* | 10/2004 | Newkirk et al. ............ 5/81.1 R |
| 2005/0000019 A1 | 1/2005 | Newkirk et al. |
| 2006/0031989 A1* | 2/2006 | Graham et al. ............ 5/610 |
| 2006/0207025 A1* | 9/2006 | Newkirk et al. ............ 5/600 |
| 2006/0207026 A1* | 9/2006 | Newkirk et al. ............ 5/600 |
| 2006/0242763 A1* | 11/2006 | Graham et al. ............ 5/503.1 |
| 2007/0069093 A1* | 3/2007 | Graham et al. ............ 248/231.71 |
| 2007/0138354 A1* | 6/2007 | Graham et al. ............ 248/121 |
| 2007/0187559 A1* | 8/2007 | Newkirk et al. ............ 248/125.8 |
| 2007/0251014 A1* | 11/2007 | Newkirk et al. ............ 5/658 |

FOREIGN PATENT DOCUMENTS

| | | |
|---|---|---|
| EP | 0 943 306 A1 | 9/1999 |
| EP | 1 243 900 A2 | 9/2002 |
| GB | 1 061 383 | 3/1967 |
| WO | WO 92/18085 | 10/1992 |
| WO | 00/09061 | 2/2000 |
| WO | WO 00/09061 | 2/2000 |

OTHER PUBLICATIONS

"Modular Pump Star", The Headwall Company, Modular Services Company, 2005, 4 pages.

Notification of Transmittal of the International Search Report from parent PCT/US04/33469.

* cited by examiner

ABLE PATIENT CARE
EQUIPMENT SUPPORT

CROSS REFERENCE TO RELATED APPLICATIONS

This application claims the benefit of U.S. Provisional Patent Application No. 60/776,768, filed Feb. 24, 2006. This application is also a continuation-in-part of and claims priority to International Application Serial No. PCT/US2004/033469 filed Oct. 12, 2004, which claims priority to a U.S. Provisional Application Ser. No. 60/510,756 filed Oct. 13, 2003. U.S. Provisional Application Nos. 60/776,768 and 60/510,756 and International Application Serial No. PCT/US2004/033469 are hereby incorporated by reference herein.

FIELD OF THE INVENTION

The present disclosure relates to a patient care equipment support, and more particularly relates to a transferable patient care equipment support

BACKGROUND OF THE INVENTION

Hospitalized patients often require patient care equipment to be in close proximity during hospital care. Such patient care equipment is typically supported on a patient care equipment support or rack. Illustratively, patient care equipment includes any one or more of the following: heart monitoring equipment, medical gas delivery equipment, infusion management equipment, intra-venous bags, equipment monitors, patient monitors, defibrillators, IV poles, and the like, many of which directly connect to the patient via lines or tubes.

It is desirable that patient care equipment is transferable between a patient support, such as a hospital bed, a stretcher, an ambulatory care chair, and the like, and a support structure, such as a ceiling or wall-mounted service column, a ceiling or wall-mounted equipment support arm, a floor-supported stand, a wheeled cart, a headwall, a wall of a hospital room, and the like.

SUMMARY OF THE INVENTION

The present invention comprises an apparatus having one or more of the features recited in the claims or one or more of the following features, which alone or in any combination may comprise patentable subject matter:

Illustratively, a transferable equipment support includes an equipment supporting portion configured to support patient care equipment and a post coupled to the equipment supporting portion and extending downwardly therefrom. Typically, the post has first and second tapered portions.

The equipment support is illustratively transferable between a first device having a first tapered socket and a second device having a second tapered socket. The first and second tapered portions of the post are configured for receipt in the first and second tapered sockets, respectively.

Illustratively, the first and second tapered portions of the post are upper and lower tapered portions and the first and second tapered sockets carried by the first and second devices are upper and lower tapered sockets. The post may include a generally cylindrical intermediate portion separating the upper and lower tapered portions. The equipment support may be rotatable about a longitudinal axis of the post when the equipment support is supported by the first and second devices.

Each tapered portion may be frustoconical with a taper in a downward direction. Illustratively, the post has an upper relatively large diameter tapered portion and a lower relatively small diameter tapered portion. Each tapered portion of the post may vary in diameter from a large diameter to a small diameter in a downward direction. The small diameter of the upper relatively large diameter tapered portion may be equal to or larger than the large diameter of the lower relatively small diameter tapered portion. The upper relatively large diameter tapered portion may comprise a tapered collar mounted on the post and movable in a longitudinal direction relative to the post.

Typically, each tapered socket has an upwardly opening frustoconical bore that varies in diameter from a large diameter to a small diameter in a downward direction. The small diameter of the bore in the upper tapered socket may be equal to or larger than the large diameter of the bore in the lower tapered socket.

Illustratively, the upper tapered socket has a generally c-shaped cross section having spaced apart end portions which define an outwardly opening slot in communication with the bore in the upper tapered socket. The spacing between the end portions of the c-shaped upper tapered socket is illustratively larger than the diameter of the generally cylindrical intermediate portion of the post. The height of the generally cylindrical intermediate portion of the post may be greater than the height of the c-shaped upper tapered socket.

Illustratively, the equipment support may be transferred from the first device to the second device as the upper tapered socket carrying the equipment support is lowered while the lower tapered portion of the post is generally aligned with the lower tapered socket to a position where the upper tapered socket is below the upper tapered portion of the post permitting the lower tapered socket to carry the equipment support and allowing the first device to move away from the second device (or the second device to move away from the first device) with the second device carrying equipment support.

Alternately or additionally, the equipment support may be transferred from the first device to the second device as the lower tapered socket is raised while the lower tapered portion of the post is generally aligned with the lower tapered socket to a position where the upper tapered portion of the post is above the upper tapered socket permitting the lower tapered socket to carry the equipment support and allowing the first device to move away from the second device (or the second device to move away from the first device) with the second device carrying equipment support.

The equipment support may be transferred from the second device to the first device as the upper tapered socket is positioned around the intermediate portion of the post and then raised to a position where the upper tapered socket engages the upper tapered portion of the post and lifts the equipment support off the lower tapered socket permitting the second device to pull away from the first device (or the first device to pull away from the second device) with the first device carrying equipment support.

Alternately or additionally, the equipment support may be transferred from the second device to the first device as the upper tapered socket is positioned around the intermediate portion of the post and then the lower tapered socket is lowered to a position where the upper tapered socket engages the upper tapered portion of the post and lifts the equipment support off the lower tapered socket permitting the second device to pull away from the first device (or the first device to pull away from the second device) with the first device carrying equipment support.

The first device may comprise one of an arm, a column, a cart, a stand, a hospital bed, a surgery table and a stretcher. The second device may comprise one of an arm, a column, a cart, a stand, a hospital bed, a surgery table and a stretcher. The equipment support may comprise a rack adapted to carry infusion equipment.

Thus, a first device may have an upper tapered socket and a second device may have a lower tapered socket. The patient care equipment support may comprise an equipment supporting portion configured to support patient care equipment and a post coupled to the equipment supporting portion and extending generally downwardly from the equipment supporting portion. Illustratively, the post has upper and lower tapered portions configured for receipt in the upper and lower tapered sockets when the equipment support is supported by the first and second devices, respectively.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the following figures, in which.

DETAILED DESCRIPTION OF THE DRAWINGS

For the purposes of promoting an understanding of the principles of the present invention, reference will be made to a number of illustrative embodiments shown in the accompanying drawings and the following description thereof.

Figures 1, 2, 4:
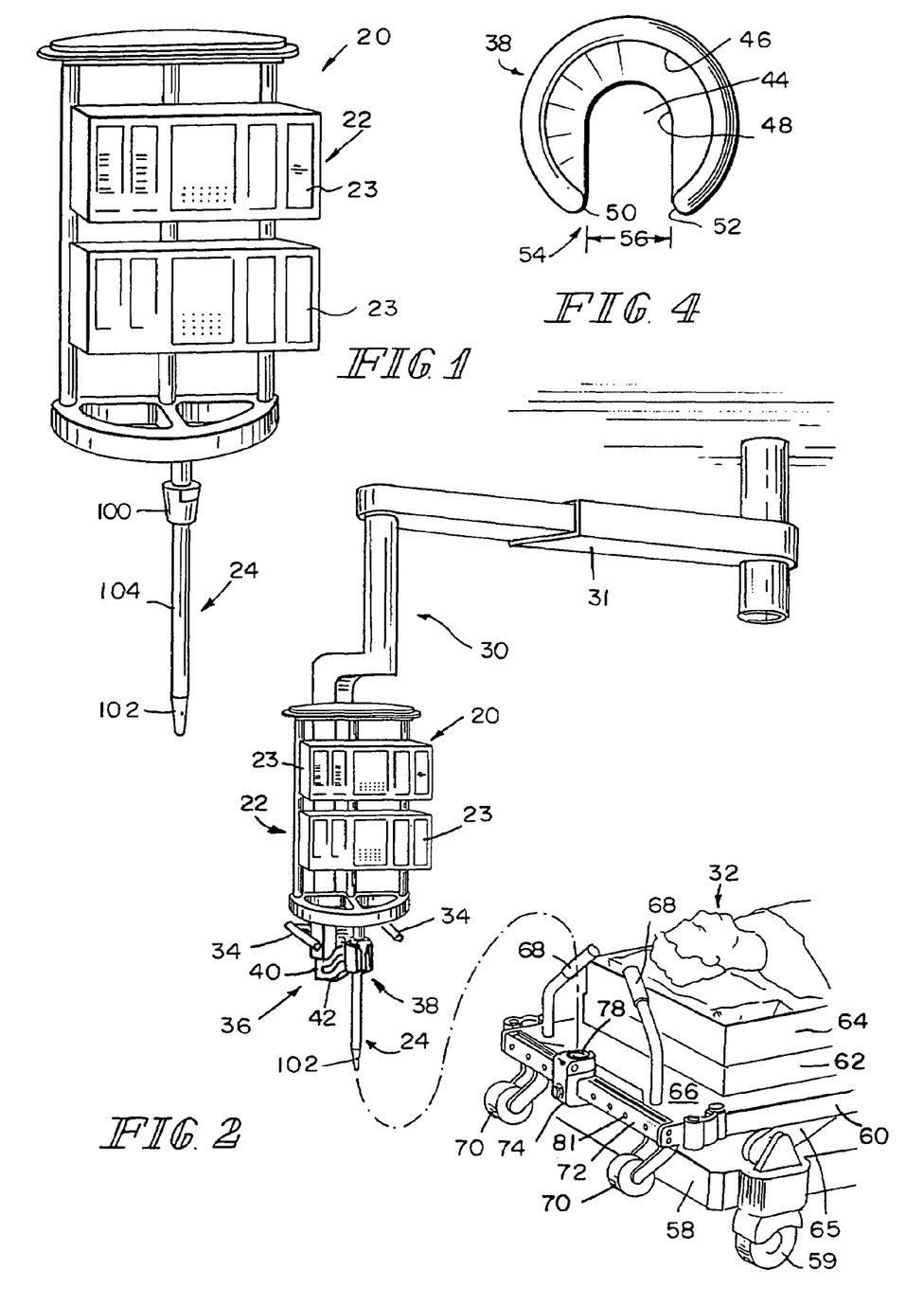
FIG. 1 is a perspective view of a transferable equipment support including an equipment supporting portion configured to support patient care equipment and a post coupled to the equipment supporting portion and extending downwardly therefrom, the post including a cylindrical intermediate portion disposed between the upper and lower tapered portions thereof.
FIG. 2 is a perspective view showing the equipment support adapted to be transferable between a service column having an upper tapered socket and a hospital bed having a lower tapered socket.
FIG. 4 is plan view of the upper tapered socket having a generally c-shaped cross section having spaced apart end portions defining an outwardly opening slot in communication with a central bore.

FIG. 1 shows an equipment support 20 having an equipment supporting portion 22 configured to support patient care equipment 23 and a post 24 (also referred to herein as "coupler") coupled to equipment supporting portion 22 and extending downwardly therefrom. Patient care equipment 23 may be any one or more of the following: heart monitoring equipment, medical gas delivery equipment, infusion management equipment, equipment monitors, patient monitors, defibrillators, IV poles, and the like, many of which are directly connected to a patient via lines or tubes.

FIG. 2 shows equipment support 20 adapted to be transferable between a support structure, such as a column 30, and a patient support, such as a hospital bed 32. In FIG. 2, the support structure is illustratively column 30 carried by a radial arm 31 mounted to a ceiling or a wall of a patient room of a hospital or a healthcare facility. However, it should be understood that the support structure may very well be a floor-supported stand, a wheeled cart or dolly, a headwall, a wall of a hospital room, and the like. Also, in FIG. 2, the patient support is illustratively hospital bed 32 positioned in a patient room of a hospital or a healthcare facility. However, it should be understood that the patient support may very well be a stretcher, a surgical table, an ambulatory care chair, and the like. Also, it should be understood that the support structure and the patient support may be used in different settings such as, for example, intensive care rooms, operating rooms and physician offices.

Figure 3:
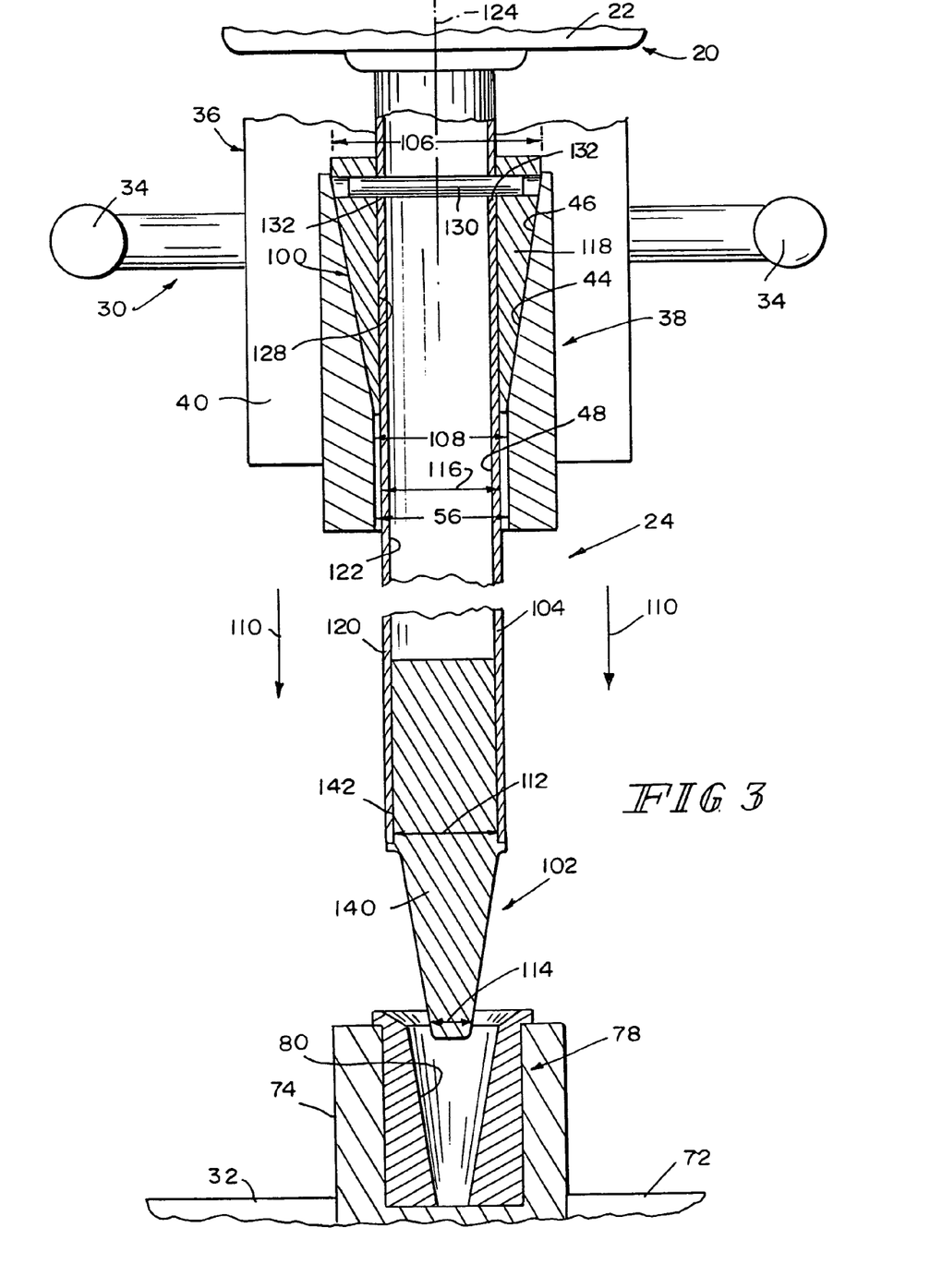
FIG. 3 is a sectional view of the upper tapered socket, the lower tapered socket and the post, and showing the post positioned over the bed-mounted lower tapered socket to transfer the equipment support from the column-mounted upper socket to the bed-mounted lower socket.

Column 30 includes a pair of handles 34, a bracket 36 and an upper tapered socket 38 (also referred to as "yoke"). Bracket 36 has a first telescoping portion 40 extending downwardly from column 30 and a second cantilevered portion 42 carrying upper socket 38. As shown in FIGS. 3 and 4, upper socket 38 has an upwardly opening bore 44. Bore 44 has an upper generally frustoconical portion 46 and a lower generally cylindrical portion 48. Upper frustoconical portion 46 varies in diameter from a large diameter to a small diameter in a downward direction. Upper socket 38 has a generally c-shaped cross section having spaced apart end portions 50, 52 which define an outwardly opening slot 54 in communication with bore 44. Spacing 56 between end portions 50, 52 of upper socket 38 is larger than the diameter 116 of a generally cylindrical intermediate portion 104 of post 24 to allow column-mounted upper socket 38 to pull away from post 24 after equipment support 20 is seated downwardly in a bed-mounted lower socket 78. Illustratively, U.S. patent application Ser. No. 10/802,287, titled "RADIAL ARM SYSTEM FOR PATIENT CARE EQUIPMENT," filed Mar. 17, 2004, now U.S. Patent Application Publication No. 2004/0232286 A1, discloses such arm-mounted column and is hereby incorporated by reference herein.

Illustratively, first portion 40 of bracket 36 telescopes vertically relative to column 30 under the power of an electric motor (not shown) housed in column 30. Electric motor may be a Linak LA 31 Linear Actuator. Electric motor may be actuated by either a toggle switch (not shown) positioned on column 30, or a wired or wireless remote control. Illustratively, bracket 36 may move as much as 30 to 45 centimeters in a vertical direction relative to column 30. Such vertical telescoping movement of bracket 36 permits equipment support 20 to be raised and lowered for optimal positioning of patient care equipment 23 relative to a patient resting on a patient support. Also, such vertical telescoping movement of bracket 36 facilitates transfer of equipment support 20 between service column 30 and hospital bed 32. Additionally, such vertical telescoping movement permits the docking of equipment support 20 with a bed-mounted socket 78, as disclosed, for example, in U.S. patent application Ser. No. 10/802,289, titled "PATIENT CARE EQUIPMENT MANAGEMENT SYSTEM," filed Mar. 17, 2004, now U.S. Patent Application Publication No. 2005/0000019 A1, which is hereby incorporated by reference herein.

Hospital bed 32 illustratively includes a lower frame 58 supported on casters 59, an upper frame 60 supported above lower frame 58 for movement relative to lower frame 58 between raised and lowered positions, a deck 62 supported above upper frame 60, and a mattress 64 supported by deck 62. An elevation adjustment mechanism 65 connects upper frame 60 to lower frame 58. Elevation adjustment mechanism 65 may be driven by a suitable actuator to cause upper frame 60 to move relative to lower frame 58. Although, upper frame 60 is movable relative to lower frame 58 in the illustrated embodiment, upper frame 60 need not be movable. Upper frame 60 includes a head-end frame member 66, which is configured to extend horizontally along the head end of upper frame 60. Illustratively, head-end frame member 66 extends beyond the outer periphery of deck 62, and supports push handles 68 and rolling bumpers 70.

A rail 72 is supported by frame member 66. A carriage 74 is coupled to rail 72 for movement along rail 72. Carriage 74 includes a lower tapered socket 78. Lower socket 78 has an upwardly opening frustoconical bore 80. As shown in FIG. 3, frustoconical bore 80 varies in diameter from a large diameter to a small diameter in a downward direction. Carriage 74 is lockable at any one of a plurality of locations 81 along rail 72. As explained below, the upward and downward movement of upper frame 60 carrying lower tapered socket 78 facilitates transfer of equipment support 20 between service column 30 and hospital bed 32 and facilitates the docking of downwardly extending post 24 of equipment support 20 with lower tapered socket 78. Illustratively, PCT Patent Application, Ser. No. US 2004/033470, titled "PATIENT CARE EQUIPMENT SUPPORT SYSTEM," filed concurrently herewith, now PCT Publication No. WO 2005/037164, discloses such hospital bed and is hereby incorporated by reference herein.

Post 24 includes a generally frustoconical upper tapered portion 100, a generally frustoconical lower tapered portion 102 and a generally cylindrical intermediate portion 104 disposed between upper and lower tapered portions 100, 102. Upper tapered portion 100 varies in diameter from a large diameter 106 to a small diameter 108 in a downward direction 110. Lower tapered portion 102 varies in diameter from a large diameter 112 to a small diameter 114 in downward direction 110. Illustratively, small diameter 108 of upper tapered portion 100 is equal to or larger than large diameter 112 of lower tapered portion 102. Diameter 116 of cylindrical intermediate portion 104 may be equal to or smaller than small diameter 108 of upper tapered portion 100. In addition, diameter 116 of cylindrical intermediate portion 104 may be equal to or larger than large diameter 112 of lower tapered portion 102.

Referring to FIG. 3, upper and lower tapered portions 100, 102 of post 24 are configured for receipt in upper and lower tapered sockets 38, 78, respectively. The height of generally cylindrical intermediate portion 104 is greater than the height of upper socket 38. Also, diameter 116 of cylindrical intermediate portion 104 is smaller than spacing 56 between end portions 50, 52 of upper socket 38. These relationships allow service column 30 to pull away from post 24 after equipment support 20 is firmly seated in lower socket 78 and upper socket 38 is lowered to a position below upper tapered portion 100.

Although, lower portion 102 of post 24 and upwardly opening bore 80 in lower socket 78 are tapered downwardly in the illustrated embodiment, lower portion 102 of post 24 and upwardly opening bore 80 in lower socket 78 need not be tapered downwardly. Instead, lower portion 102 of post 24 and upwardly opening bore 80 in lower socket 78 may be generally cylindrical.

As shown in FIG. 3, post 24 includes an outer tube 120 having a bore 122 defining a longitudinal axis 124. Upper portion 100 comprises a tapered collar 118 having a central bore 128. Upper portion 100 is sleeved over outer tube 120 for longitudinal movement relative thereto. A radially extending upper pin 130, coupled to upper portion 100, is received in a pair of oppositely disposed pin-receiving openings 132 in outer tube 120. Lower portion 102 of post 24 includes a plug 140 inserted into a lower end 142 of outer tube 120.

To transfer equipment support 20 from column 30 to bed 32, column 30 is moved to a position where lower tapered portion 102 of post 24 is generally aligned over bed-mounted lower tapered socket 78 and upper tapered socket 38 carried by column 30 is lowered to a position where equipment support 20 is seated firmly in bed-mounted lower tapered socket 78 and upper tapered socket 38 is positioned below upper tapered portion 100 of post 24. Column 30 can then be pulled away from bed 32 (or bed 32 pulled away from column 30) by virtue of the fact that slot 54 in column-mounted upper socket 38 is wider than diameter 116 of cylindrical intermediate portion 104 of post 24.

Alternately or additionally, to transfer equipment support 20 from column 30 to bed 32, column 30 is moved to a position where lower tapered portion 102 of post 24 is generally aligned over lower tapered socket 78 carried by upper frame 60 of bed 32 and upper frame 60 is raised. As upper frame 60 moves upwardly, lower tapered portion 102 of post 24 enters lower tapered socket 78 and, when this initially occurs, upper tapered portion 100 of post 24 is still received in upper tapered socket 38 carried by column 30. Further upward movement of upper frame 60 causes lower tapered portion 102 of post 24 to seat firmly in lower tapered socket 78 and causes upper tapered portion 100 of post 24 to lift upwardly out of upper tapered socket 38. After upper tapered portion 100 is raised sufficiently relative to upper tapered socket 38, column 30 can then be pulled away from bed 32 (or bed 32 pulled away from column 30) with bed 32 carrying equipment support 20. In such embodiments, where raising of upper frame 60 effects transfer of equipment support 20 from column 30 to bed 32, column 30 need not have a telescoping bracket 36 or other mechanism for raising and lowering upper tapered socket 38.

To transfer equipment support 20 from bed 32 to column 30, the sequence of steps is reversed. Column 30 is moved to a position where column-mounted upper socket 38 is positioned around intermediate portion 104 of post 24 and then raised to a position where upper socket 38 engages upper tapered portion 100 of post 24 and lifts equipment support 20 off lower socket 78 permitting column 30 to move away from bed 32 (or bed 32 to move away from column 30). Cylindrical intermediate portion 104 of post 24 is allowed to enter bore 44 in column-mounted upper tapered socket 38 through slot 54 therein. Again this is possible since slot 54 in upper tapered socket 38 is wider than diameter 116 of cylindrical intermediate portion 104 of post 24.

Alternately or additionally, to transfer equipment support 20 from bed 32 to column 30, the sequence of steps is reversed. Column 30 is moved to a position where upper tapered socket 38 carried by column 30 is positioned around intermediate portion 104 of post 24 and then upper frame 60 of bed 32 carrying lower tapered socket 78 is lowered. As upper frame 60 moves downwardly, upper tapered portion 100 of post 24 enters upper tapered socket 38 and, when this initially occurs, lower tapered portion 102 of post 24 is still received in lower tapered socket 78. Further downward movement of upper frame 60 causes upper tapered portion 100 of post 24 to seat firmly in upper tapered socket 38 and causes lower tapered portion 102 of post 24 to lift upwardly out of lower tapered socket 78. After lower tapered socket 78 is lowered sufficiently relative to lower tapered portion 102, column 30 can then be pulled away from bed 32 (or bed 32 pulled away from column 30) with column 30 carrying equipment support 20. In such embodiments, where lowering of upper frame 60 effects transfer of equipment support 20 from bed 32 to column 30, column 30 need not have a telescoping bracket 36 or other mechanism for raising and lowering upper tapered socket 38.

Figure 5:
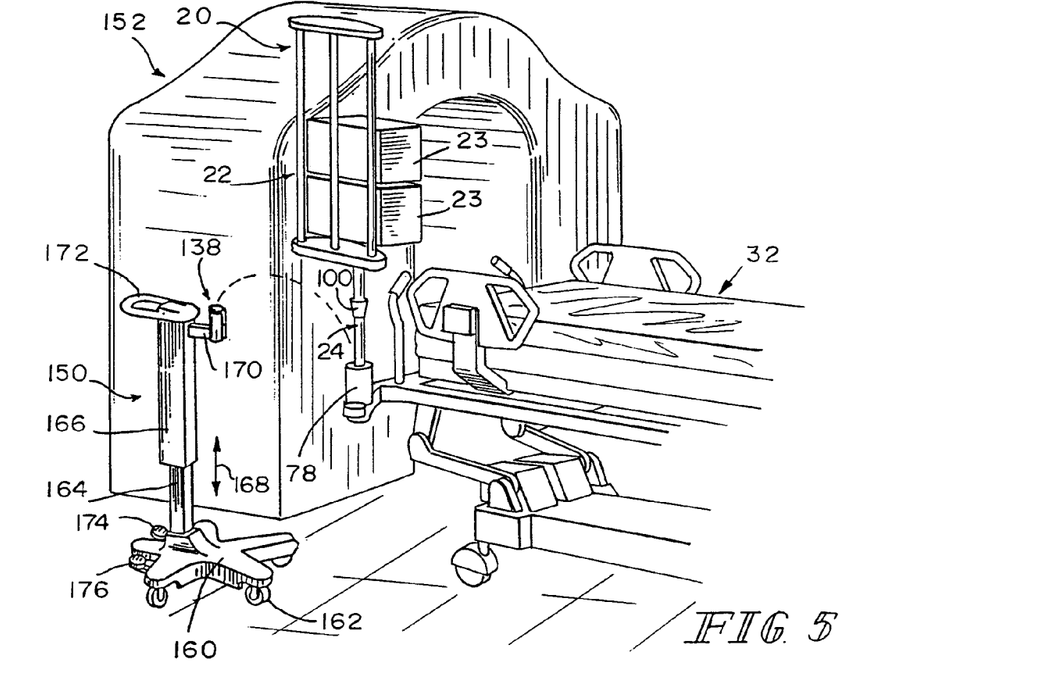
FIG. 5 is a perspective view of the equipment support carried by the bed positioned next to an equipment support cart and a CT scanner.

FIG. 5 is a perspective view of equipment support 20 carried by hospital bed 32 positioned next to an equipment support cart 150 and a CT scanner 152. Cart 150 includes a base 160 having wheels 162, a post 164 extending upwardly from base 160, a telescoping column 166 that telescopes relative to post 164 in a vertical direction 168, a bracket 170 coupled to column 166 and carrying an upper tapered socket 138, a handle 172 coupled to column 166, a lift pedal 174 to extend telescoping column 166 upwardly and a release pedal 176 to retract telescoping column 166 downwardly. Bearings (not shown) may be provided to facilitate telescoping movement of column 166 relative to post 164. Illustratively, column 166 may have between 30 centimeters and 45 centimeters of telescoping movement in vertical direction 168.

Construction of upper socket 138 shown in FIG. 5 is similar to upper socket 38 shown in FIGS. 2-4. Thus, upper socket 138 has an upwardly opening bore. The bore in upper socket 138 has an upper generally frustoconical portion and a lower generally cylindrical portion. The upper frustoconical portion in upper socket 138 varies in diameter from a large diameter to a small diameter in a downward direction. Upper socket 138 has a generally c-shaped cross section having spaced apart end portions which define an outwardly opening slot in communication with the bore therein. Spacing between the end portions of upper socket 138 is larger than the diameter 116 of a generally cylindrical intermediate portion 104 of post 24 to allow cart-mounted upper socket 138 to pull away from post 24 after equipment support 20 is seated downwardly in bed-mounted lower socket 78. Illustratively, U.S. patent application Ser. No. 10/802,289, titled "PATIENT CARE EQUIPMENT MANAGEMENT SYSTEM," filed Mar. 17, 2004, now U.S. Patent Application Publication No. 2005/0000019 A1, discloses such equipment support cart and is hereby incorporated by reference herein.

When it is desired to transfer equipment support 20 from bed 32 to cart 150, cart 150 is moved to a position where cart-mounted upper socket 138 is positioned around intermediate portion 104 of post 24 and then lift pedal 174 is actuated to extend telescoping column 166 to, in turn, raise upper socket 138 to a position where upper socket 138 engages upper tapered portion 100 of post 24 and lifts equipment support 20 off bed-mounted lower socket 78 permitting cart 150 to move away from bed 32 (or bed 32 to move away from cart 150). Cylindrical intermediate portion 104 of post 24 is allowed to enter bore in cart-mounted upper socket 138 through the slot therein. Again this is possible since the slot in upper socket 138 is wider than diameter 116 of cylindrical intermediate portion 104 of post 24.

Alternately or additionally, when it is desired to transfer equipment support 20 from bed 32 to cart 150, cart 150 is moved to a position where upper tapered socket 138 carried by cart 150 is positioned around intermediate portion 104 of post 24 and then upper frame 60 of bed 32 carrying lower tapered socket 78 is lowered. As upper frame 60 moves downwardly, upper tapered portion 100 of post 24 enters upper tapered socket 138 and, when this initially occurs, lower tapered portion 102 of post 24 is still received in lower tapered socket 78. Further downward movement of upper frame 60 causes upper tapered portion 100 of post 24 to seat firmly in upper tapered socket 138 and causes lower tapered portion 102 of post 24 to lift upwardly out of lower tapered socket 78. After lower tapered socket 78 is lowered sufficiently relative to lower tapered portion 102, cart 150 can then be pulled away from bed 32 (or bed 32 pulled away from cart 150) with cart 150 carrying equipment support 20. In such embodiments, where lowering of upper frame 60 effects transfer of equipment support 20 from bed 32 to cart 150, cart 150 need not have a telescoping column 166 or other mechanism for raising and lowering upper tapered socket 138.

When it is desired to transfer equipment support 20 from cart 150 to bed 32, the sequence of steps is reversed. Cart 150 is moved to a position where lower tapered portion 102 of post 24 is over bed-mounted lower socket 78 and a release pedal 176 is depressed. Illustratively, release pedal 174 releases a pneumatic piston inside telescoping column 166 of cart 150, thereby allowing column 166 to retract under its own weight so that lower tapered portion 102 of post 24 is seated downwardly in socket 78 of bed 32. Once lower tapered portion 102 of post 24 is seated firmly in bed-mounted socket 78, cart-mounted upper socket 138 can be lowered to a position below upper tapered portion 100 of post 24 to permit cart 150 to pull away from bed 32 (or bed 32 to pull away from cart 150).

Alternately or additionally, to transfer equipment support 20 from cart 150 to bed 32, cart 150 is moved to a position where lower tapered portion 102 of post 24 is generally aligned over lower tapered socket 78 carried by upper frame 60 of bed 32 and upper frame 60 is raised. As upper frame 60 moves upwardly, lower tapered portion 102 of post 24 enters lower tapered socket 78 and, when this initially occurs, upper tapered portion 100 of post 24 is still received in upper tapered socket 138 carried by cart 150. Further upward movement of upper frame 60 causes lower tapered portion 102 of post 24 to seat firmly in lower tapered socket 78 and causes upper tapered portion 100 of post 24 to lift upwardly out of upper tapered socket 138. After upper tapered portion 100 is raised sufficiently relative to upper tapered socket 138, cart 150 can then be pulled away from bed 32 (or bed 32 pulled away from cart 150) with bed 32 carrying equipment support 20. In such embodiments, where raising of upper frame 60 effects transfer of equipment support 20 from cart 150 to bed 32, cart 150 need not have a telescoping column 166 or other mechanism for raising and lowering upper tapered socket 138.

Figure 6:
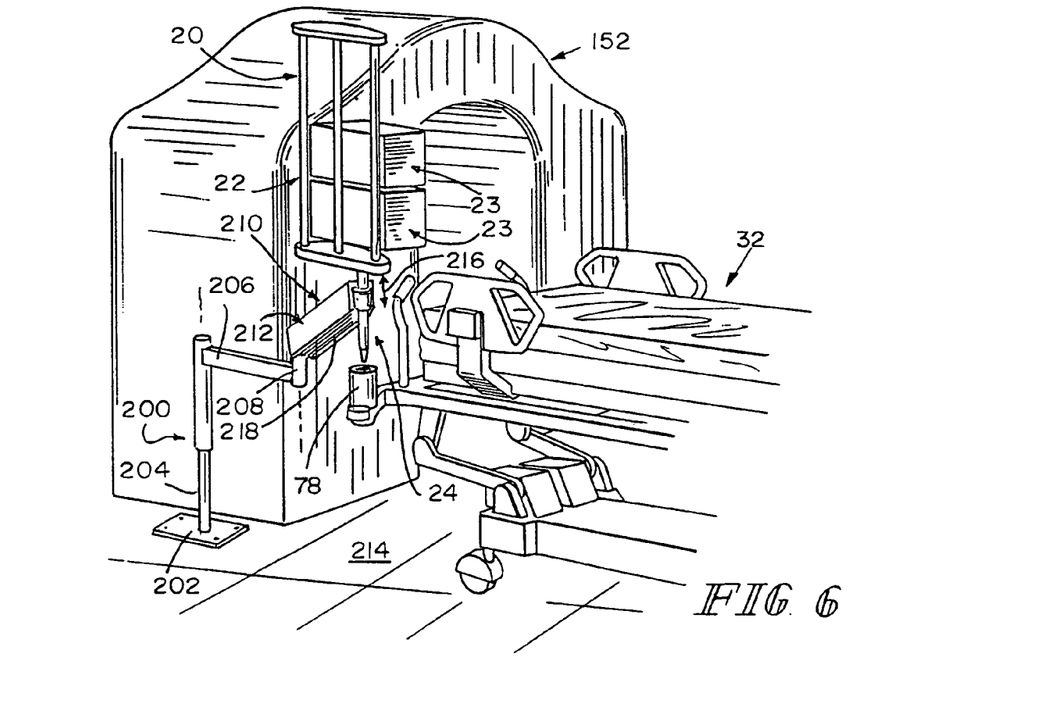
FIG. 6 is a perspective view similar to FIG. 5 showing the equipment support carried by a floor-mounted stand positioned next to the bed and the CT scanner.

FIG. 6 is a perspective view of equipment support 20 carried by a floor-supported stand 200 positioned next to hospital bed 32 and CT scanner 152. Stand 200 includes a base 202, a post 204 extending upwardly from base 202, a cantilevered telescopic arm 206 having a proximal end coupled to post 204 and extending horizontally away from post 204, a mount 208 coupled to a distal end of arm 206 and a 4-bar motorized lift 210 coupled to mount 208. Lift 210 carries an upper tapered socket 238. Actuator buttons 212 are located on lift 210 which can be depressed by a caregiver desiring to either raise or lower upper socket 238 relative to a floor 214 of the hospital room. Illustratively, lift 210 may have between 30 centimeters and 45 centimeters of movement in vertical direction 216.

Construction of upper socket 238 shown in FIG. 6 is similar to upper sockets 38, 138 shown in FIGS. 2-5. Thus, upper socket 238 has an upwardly opening bore. The bore in upper socket 238 has an upper generally frustoconical portion and a lower generally cylindrical portion. The upper frustoconical portion in upper socket 238 varies in diameter from a large diameter to a small diameter in a downward direction. Upper socket 238 has a generally c-shaped cross section having spaced apart end portions which define an outwardly opening slot in communication with the bore therein. Spacing between the end portions of upper socket 238 is larger than the diameter 116 of a generally cylindrical intermediate portion 104 of post 24 to allow stand-mounted upper socket 238 to swing away from post 24 after equipment support 20 is seated downwardly in bed-mounted lower socket 78.

Illustratively, lift 210 comprises a top frame member and a bottom frame member. Each frame member is illustratively a U-shaped metal frame. At one end, the top and bottom frame members are each pivotably attached to mount 208. At the other end, the top and bottom frame members are each pivotably attached to upper socket 238. The top and bottom frame members, mount 208 and upper socket 238 form a parallelogram linkage. A linear actuator 218 is pivotably coupled at one end to the bottom frame member, and at the other end to the top frame member.

Illustratively, as linear actuator 218 extends, lift 210 is moved from a lowered position to a raised position. As linear actuator 218 retracts, lift 210 is moved from a raised position to a lowered position. Upper socket 238 remains vertically oriented as lift 210 is raised and lowered because of the parallelogram linkage coupling upper socket 238 to mount 208. Linear actuator 218 is illustratively Linak LA 28 Linear Actuator. Although linear actuator 218 is an electrically powered linear motor, it is within the scope of the disclosure to utilize any electric, pneumatic, gas powered, or other type of motor that is capable of lifting one end of a motorized lift relative to the other end. Illustratively, U.S. patent application Ser. No. 10/802,289, titled "PATIENT CARE EQUIPMENT MANAGEMENT SYSTEM," filed Mar. 17, 2004, now U.S. Patent Application Publication No. 2005/0000019 A1, discloses such floor-supported stand, and is hereby incorporated by reference herein.

When it is desired to transfer equipment support 20 from stand 200 to bed 32, telescoping arm 206 is moved to a position where lower tapered portion 102 of post 24 is over bed-mounted socket 78. Lift 210 is then actuated to lower upper socket 238 carrying equipment support 20 to a position where equipment support 20 is seated firmly in bed-mounted socket 78. Once equipment support 20 is seated firmly in bed-mounted socket 78, upper socket 238 can be lowered to a position below upper tapered portion 100 of post 24 to permit telescoping arm 206 to retract and swing away from bed 32 (or bed 32 to move way from stand 200).

Alternately or additionally, to transfer equipment support 20 from stand 200 to bed 32, telescoping arm 206 is moved to a position where lower tapered portion 102 of post 24 is generally aligned over lower tapered socket 78 carried by upper frame 60 of bed 32 and upper frame 60 is raised. As upper frame 60 moves upwardly, lower tapered portion 102 of post 24 enters lower tapered socket 78 and, when this initially occurs, upper tapered portion 100 of post 24 is still received in upper tapered socket 238 carried by stand 200. Further upward movement of upper frame 60 causes lower tapered portion 102 of post 24 to seat firmly in lower tapered socket 78 and causes upper tapered portion 100 of post 24 to lift upwardly out of upper tapered socket 238. After upper tapered portion 100 is raised sufficiently relative to upper tapered socket 238, telescoping arm 206 can then retract and swing away from bed 32 (or bed 32 can move away from stand 200) with bed 32 carrying equipment support 20. In such embodiments, where raising of upper frame 60 effects transfer of equipment support 20 from stand 200 to bed 32, stand 200 need not have a lift 210 or other mechanism for raising and lowering upper tapered socket 238.

When it is desired to transfer equipment support 20 from bed 32 to stand 200, the sequence of steps is reversed. Arm 206 is moved to a position where upper tapered socket 238 is positioned around intermediate portion 104 of post 24. Lift 210 is then actuated to raise upper socket 238 to a position where upper tapered socket 238 engages upper tapered portion 100 of post 24 and lifts equipment support 20 off bed-mounted lower socket 78 permitting bed 32 to move away from stand 200. Cylindrical intermediate portion 104 of post 24 is allowed to enter the bore in upper tapered socket 238 through the slot therein since the slot in upper tapered socket 238 is wider than diameter 116 of cylindrical intermediate portion 104 of post 24.

Alternately or additionally, when it is desired to transfer equipment support 20 from bed 32 to stand 200, telescoping arm 206 is moved to a position where upper tapered socket 238 carried by lift 210 is positioned around intermediate portion 104 of post 24 and then upper frame 60 of bed 32 carrying lower tapered socket 78 is lowered. As upper frame 60 moves downwardly, upper tapered portion 100 of post 24 enters upper tapered socket 238 and, when this initially occurs, lower tapered portion 102 of post 24 is still received in lower tapered socket 78. Further downward movement of upper frame 60 causes upper tapered portion 100 of post 24 to seat firmly in upper tapered socket 238 and causes lower tapered portion 102 of post 24 to lift upwardly out of lower tapered socket 78. After lower tapered socket 78 is lowered sufficiently relative to lower tapered portion 102, telescoping arm 206 can then retract and swing away from bed 32 (or bed 32 can move away from stand 200) with stand 200 carrying equipment support 20. In such embodiments, where lowering of upper frame 60 effects transfer of equipment support 20 from bed 32 to stand 200, stand 200 need not have a lift 210 or other mechanism for raising and lowering upper tapered socket 238.

Although the invention has been described in detail with reference to certain illustrative embodiments, variations and modifications exist with the scope and spirit of this disclosure as described and defined in the following claims.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

There are a plurality of advantages of the present invention arising from the various features of the embodiments described herein. It will be noted that alternative embodiments of the present invention may not include all of the features described yet still benefit from at least some of the advantages of such features. Those of ordinary skill in the art may readily devise their own implementations of a device that incorporates one or more of the features of the present invention and fall within the spirit and scope of the present invention as defined by the appended claims.

The invention claimed is:

1. An apparatus comprising:
a first device having an upper tapered socket,
a second device having a lower tapered socket,
wherein each socket has an upwardly opening frustoconical bore that varies in diameter from a larger diameter to a smaller diameter in a downward direction,
wherein the smaller diameter of the bore in the upper tapered socket is equal to or larger than the larger diameter of the bore in the lower tapered socket, and
a patient care equipment support comprising:

an equipment supporting portion configured to support patient care equipment, and a post coupled to the equipment supporting portion such that the post extends generally downwardly from the equipment supporting portion, the post having upper and lower tapered portions, the upper tapered portion being configured for receipt in the upper tapered socket when the equipment support is supported by the first device and the lower tapered portion being configured for receipt in the lower tapered socket when the equipment support is supported by the second device wherein each tapered portion is frustoconical, each tapered portion varies in diameter from a larger diameter to a smaller diameter in a downward direction, and the smaller diameter of the upper tapered portion is equal to or larger than the larger diameter of the lower tapered portion, wherein the post has a generally cylindrical intermediate portion separating the two tapered portions, and wherein the upper tapered socket has a generally c-shaped cross section having spaced apart end portions which define an outwardly opening slot in communication with the bore in the upper tapered socket, and the spacing between the end portions of the c-shaped upper tapered socket is larger than the diameter of the generally cylindrical intermediate portion.

2. The apparatus of claim 1, wherein the height of the generally cylindrical intermediate portion is greater than the height of the c-shaped upper tapered socket.

3. The apparatus of claim 2, wherein the equipment support is transferred from the first device to the second device as the upper tapered socket carrying the equipment support is lowered while the lower tapered portion of the post is generally aligned with the lower tapered socket to a position where the upper tapered socket is below the upper tapered portion of the post permitting the lower tapered socket to carry the equipment support and allowing the first device to move away from the second device.

4. The apparatus of claim 2, wherein the equipment support is transferred from the first device to the second device by raising the lower tapered socket a first amount while the lower tapered portion of the post is generally aligned with the lower tapered socket such that the lower tapered portion enters the lower tapered socket and, then by raising the lower tapered socket a second amount to lift the upper tapered portion of the post out of the upper tapered socket permitting the lower tapered socket to carry the equipment support and allowing the first device to move away from the second device.

5. The apparatus of claim 2, wherein the equipment support is transferred from the second device to the first device as the upper tapered socket is positioned around the intermediate portion of the post and then raised to a position where the upper tapered socket engages the upper tapered portion of the post and lifts the equipment support off the lower tapered socket permitting the second device to move away from the first device.

6. The apparatus of claim 2, wherein the equipment support is transferred from the second device to the first device by lowering the lower tapered socket a first amount while the upper tapered socket is positioned around the intermediate portion of the post such that upper tapered portion enters the upper tapered socket and, then by lowering the lower tapered socket a second amount to lift the lower tapered portion of the post out of the lower tapered socket permitting the upper tapered socket to carry the equipment support and allowing the first device to move away from the second device.

7. A patient care equipment support apparatus comprising a first tapered socket having a generally c-shaped cross section defining an outwardly opening slot in communication with the bore of the socket, the socket including an upwardly opening frustoconical bore that varies in diameter from a larger diameter to a smaller diameters an equipment supporting portion, and a coupler coupled to the equipment supporting portion, the coupler extending generally downwardly from the equipment supporting portion and having a first tapered portion and a second tapered portion having an upper end spaced apart from and below a lower end of the first tapered portion, each tapered portion of the coupler being configured for receipt in the first tapered socket.

8. The apparatus of claim 7, wherein the coupler has a generally cylindrical intermediate portion separating the two tapered portions.

9. The apparatus of claim 8 wherein the c-shaped cross section of the first socket is sized to permit the cylindrical portion of the coupler to pass through the opening slot when the coupler is engaged with a socket.

10. The apparatus of claim 9 wherein each of the tapered portions of the coupler is frustoconical.

11. The apparatus of claim 7, wherein the coupler is a downwardly extending post.

12. The apparatus of claim 7, wherein the equipment support apparatus comprises one of an IV pole and a rack adapted to carry infusion equipment.

13. The apparatus of claim 7 wherein apparatus further comprises a motor configured to raise and lower the first tapered socket.

14. The apparatus of claim 7 wherein the apparatus comprises an outer telescoping portion and an inner telescoping portion nested within the outer telescoping portion configured to raise and lower the first tapered socket.

15. The apparatus of claim 7 comprising a second tapered socket spaced apart from the first tapered socket, the second tapered socket including upwardly opening frustoconical bore that varies in diameter from a larger diameter to a smaller diameter.

16. The apparatus of claim 15 wherein the apparatus comprises a first device supporting the first tapered socket and a second device supporting the second tapered socket.

17. The apparatus of claim 16 wherein at least one of the first and second devices comprises a motor configured to raise and lower one of the first and second tapered sockets.

18. The apparatus of claim 16, wherein the upper tapered portion of the coupler and the first tapered socket are configured such that the equipment support apparatus is rotatable about a longitudinal axis of the coupler when the equipment support is supported by the first device, and the lower tapered portion of the coupler and the second tapered socket are configured such that the equipment support apparatus is rotatable about the longitudinal axis of the coupler when the equipment support is supported by the second device.

19. The apparatus of claim 16, wherein the first device comprises one of an arm, a column, a cart, a stand, a hospital bed, a surgery table and a stretcher.

20. The apparatus of claim 16, wherein the second device comprises one of an arm, a column, a cart, a stand, a hospital bed, a surgery table and a stretcher.

21. The apparatus of claim 7 wherein each of the tapered portions of the coupler is frustoconical.

* * * * *